United States Patent
Zhang et al.

(10) Patent No.: US 12,171,546 B2
(45) Date of Patent: Dec. 24, 2024

(54) ULTRAFAST TRACER IMAGING FOR POSITRON EMISSION TOMOGRAPHY

(71) Applicant: The Regents of the University of California, Oakland, CA (US)

(72) Inventors: Xuezhu Zhang, Davis, CA (US); Jinyi Qi, Davis (CA); Simon R. Cherry, Davis, CA (US); Ramsey D. Badawi, Sacramento, CA (US); Guobao Wang, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 401 days.

(21) Appl. No.: 17/619,471

(22) PCT Filed: Jul. 16, 2020

(86) PCT No.: PCT/US2020/042401
§ 371 (c)(1),
(2) Date: Dec. 15, 2021

(87) PCT Pub. No.: WO2021/011815
PCT Pub. Date: Jan. 21, 2021

(65) Prior Publication Data
US 2022/0304596 A1    Sep. 29, 2022

Related U.S. Application Data

(60) Provisional application No. 62/875,329, filed on Jul. 17, 2019.

(51) Int. Cl.
*A61B 5/11* (2006.01)
*A61B 5/00* (2006.01)
(Continued)

(52) U.S. Cl.
CPC ........ *A61B 5/1128* (2013.01); *A61B 5/02755* (2013.01); *A61B 5/113* (2013.01);
(Continued)

(58) Field of Classification Search
CPC ... A61B 5/1128; A61B 5/02755; A61B 5/113; A61B 5/7289; A61B 6/037; A61B 6/486; G01T 1/2985
See application file for complete search history.

(56) References Cited

U.S. PATENT DOCUMENTS

2010/0290683 A1*  11/2010  Demeester ............... A61B 5/33
                                                                                    382/131
2017/0103551 A1*   4/2017  Sun ....................... G06T 11/005

FOREIGN PATENT DOCUMENTS

WO   WO-2018172229 A1 *  9/2018  ............ A61B 5/08
WO   WO-2019136469 A1 *  7/2019  ............ A61B 6/037

* cited by examiner

*Primary Examiner* — Wednel Cadeau
(74) *Attorney, Agent, or Firm* — Park, Vaughan, Fleming & Dowler LLP (57) ABSTRACT

The disclosed embodiments relate to a system that performs ultra-fast tracer imaging on a subject using positron emission tomography. During operation, the system performs a high-temporal-resolution, total-body dynamic PET scan on the subject as an intravenously injected radioactive tracer propagates through the vascular system of the subject to produce PET projection data. Next, the system applies an image reconstruction technique to the PET projection data to produce subsecond temporal frames, which illustrate the dynamic propagation of the radioactive tracer through the vascular system of the subject. Finally, the system outputs the temporal frames through a display device.

29 Claims, 6 Drawing Sheets

(51) Int. Cl.
*A61B 5/0275* (2006.01)
*A61B 5/113* (2006.01)
*A61B 6/00* (2024.01)
*A61B 6/03* (2006.01)
*G01T 1/29* (2006.01)

(52) U.S. Cl.
CPC ............ *A61B 5/7289* (2013.01); *A61B 6/037* (2013.01); *A61B 6/486* (2013.01); *G01T 1/2985* (2013.01)

ULTRAFAST TRACER IMAGING FOR POSITRON EMISSION TOMOGRAPHY

CROSS-REFERENCE TO RELATED APPLICATION

This application claims the benefit of U.S. Provisional Patent Application Ser. No. 62/875,329, entitled "Ultra-Fast Tracer Imaging Using Positron Emission Tomography," by inventors Xuezhu Zhang, et al., filed on 17 Jul. 2019, the contents of which are incorporated by reference herein.

GOVERNMENT LICENSE RIGHTS

This invention was made with U.S. government support under grant number R01-CA206187 awarded by the National Institutes of Health (NIH) National Cancer Institute (NCI). The U.S. government has certain rights in the invention.

BACKGROUND

Field

The disclosed embodiments generally relate to techniques for performing positron emission tomography (PET). More specifically, the disclosed embodiments relate to techniques for performing ultra-fast tracer imaging in a PET scanning system.

Related Art

Imaging systems based on PET have been widely applied in medical fields, such as oncology, neurology, and cardiology. These imaging systems facilitate sensitive molecular imaging of biological processes using radiotracers, which are introduced into a subject's bloodstream. By dynamically acquiring images over time, PET systems can measure the spatiotemporal distribution of radiotracers in vivo, which can be used to provide assays of physiologically and biologically relevant information, such as cerebral blood volume, blood flow, glucose metabolism, oxygen use, DNA synthesis, signal transduction, immune system activation, cancer cell phenotyping for molecularly targeted therapies, pharmacokinetics, and pharmacodynamics, through mathematic modeling of the tracer kinetics.

However, existing PET scanning techniques have a number of shortcomings, which make it challenging for existing PET scanning systems to monitor blood flow dynamics in real time. First, the limited temporal resolution of existing PET scanning systems and associated image reconstruction techniques makes it difficult (if not impossible) to visualize blood flow dynamics at subsecond time scales. This makes it hard to analyze blood flow behavior during individual heart beats.

Second, because of the limited length of existing PET scanners (e.g., typically covering an axial field of view of 15-30 cm), most dynamic PET scans have been restricted to a single bed position over a limited region of the human body. To acquire whole-body dynamic images (e.g., typically from head or neck to upper thigh), multiple-bed-position scans with a sequential multi-pass protocol have been introduced. However, the resulting temporal sampling resolution is limited by multiple-bed position acquisition, and fast tracer dynamics cannot be captured except in a single body region. Moreover, the scan duration is divided among multiple bed positions, resulting in reduced sensitivity and a low signal-to-noise ratio for parametric imaging.

Hence, what is needed is a new PET scanning system, which does not suffer from the above-described temporal resolution limitations and length limitations of existing PET systems.

SUMMARY

The disclosed embodiments relate to a system that performs ultra-fast tracer imaging on a subject using positron emission tomography. During operation, the system performs a high-temporal-resolution, total-body dynamic PET scan on the subject as an intravenously injected radioactive tracer propagates through the vascular system of the subject to produce PET projection data. Next, the system applies an image reconstruction technique to the PET projection data to produce subsecond temporal frames, which illustrate the dynamic propagation of the radioactive tracer through the vascular system of the subject. Finally, the system outputs the temporal frames through a display device.

In some embodiments, the high temporal resolution of the subsecond temporal frames facilitates visualizing the dynamics of tracer propagation through the vascular system of the subject during individual heart beats.

In some embodiments, the subsecond temporal frames comprise 100 millisecond temporal frames.

In some embodiments, the reconstruction technique extracts dynamic image features in the temporal frames.

In some embodiments, while applying the image reconstruction technique to the PET projection data, the system uses a statistically based technique to iteratively reconstruct the temporal frames from the PET projection data.

In some embodiments, the statistically based technique includes one or more of the following: a maximum-likelihood estimation technique; a penalized-likelihood estimation technique; a regularization technique; and a post-filtering technique.

In some embodiments, while applying the image reconstruction technique to the PET projection data, the system uses a kernel-based regularization technique with an associated kernel function to construct a kernel matrix. Next, the system uses the kernel matrix to reconstruct the subsecond temporal frames based on the PET projection data.

In some embodiments, the kernel-based regularization technique reconstructs a current temporal frame based on PET projection data associated with future temporal frames.

In some embodiments, while performing the image reconstruction technique, the system uses a machine-learning-based de-noising technique to de-noise low-count images and/or iteratively reconstruct the temporal frames.

In some embodiments, the system additionally extracts a motion signal associated with cardiac, respiratory, and/or body motion from the reconstructed temporal frames and/or associated dynamic projections. Next, the system uses a filter to smooth the extracted motion signal, and the smoothed motion signal is subsequently used to perform motion gating on the reconstructed temporal frames.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Overview

The disclosed embodiments provide an ultra-high temporal resolution reconstruction technique for use on PET scanners, which can achieve dynamic PET imaging with a temporal resolution of 100 ms or less. This technique has applications in studying fast tracer dynamics, such as blood flow and dynamic response to neural modulation, as well as performing real-time motion tracking (e.g., cardiac and respiratory motion, body motion) without an external device (e.g., no ECG, breathing belt, or optical markers). This technique operates by applying a newly developed, kernel-regularized reconstruction technique to PET scanner data. (For a description of this reconstruction technique, see G. Wang, J. Qi, PET image reconstruction using kernel method. *IEEE Trans. Med. Imaging* 34, 61-71, 2015.) By using this technique, it is possible to capture the dynamics of initial tracer distribution and cardiac motion with high temporal resolution.

To demonstrate the effectiveness of this technique, we tested on a one-hour total-body dynamic PET scan acquired during and following an intravenous injection of 256 MBq of 18F-FDG. We divided the dataset into 100 millisecond temporal frames and analyzed the data in the first and last minutes of the scan, which represent the fast tracer transit and tracer uptake at equilibrium status, respectively. Dynamic data was reconstructed using the kernel-based reconstruction technique with quantitative corrections. The resulting reconstructed images were high quality. In fact, cardiac motion is clearly visible in the 100 millisecond temporal frames. Moreover, the extracted time activity curves from major vascular regions of interest show the dynamic change of tracer distribution in the left ventricle and major arteries during cardiac contraction and expansion.

Furthermore, a cardiac motion signal was extracted directly from the data-driven reconstructed images and was used to perform cardiac gating, which enhances patient comfort without requiring an external monitoring device (e.g., ECG, breathing belt, optical markers, etc.). Reconstructed gated images using this kernel method exhibit a better contrast-versus-background-noise tradeoff than the standard ordered subset expectation-maximization reconstruction technique.

Hence, we have successfully developed a new methodology for total-body high-temporal-resolution dynamic PET. This innovation demonstrates that the kernel-regularized reconstruction techniques can achieve superior image quality for motion-frozen quantitative studies for PET. In addition to the kernel technique, machine learning can also be used in combination with current reconstruction techniques to improve the image quality.

This new technique has applications in real-time blood flow tracking over the human circulatory system, and motion-freeze (heart beating/breathing) monitoring for cardiovascular and cerebrovascular diseases, and respiratory system function diagnosis. Moreover, this new technique can be applied to any clinical PET system for marker-free, motion-free, real-time fast tracer tracking. Hence, this new technique can provide high-quality images for tracking fast tracer dynamics, such as blood flow and dynamic response to neural modulation, as well as perform real-time motion tracking (e.g., cardiac and respiratory motion, body motion) without requiring an external device to obtain motion-frozen images for cardiovascular and respiratory system function diagnosis.

Before describing this new technique further, we first describe an exemplary PET scanning system in which it can operate.

System

Figure 1:
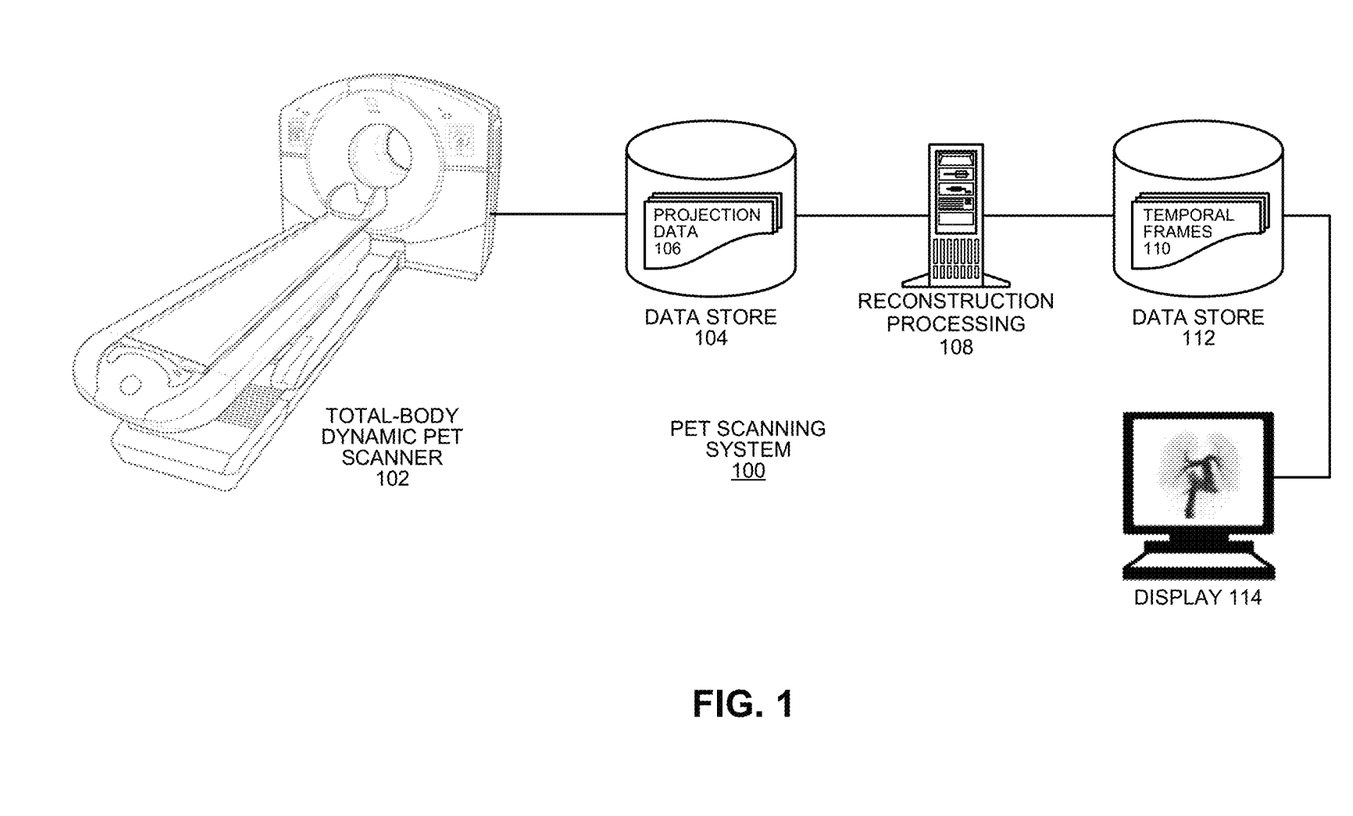
FIG. 1 illustrates a PET scanning system that supports subsecond total-body imaging in accordance with the disclosed embodiments.

FIG. 1 illustrates a PET scanning system 100 that supports subsecond total-body imaging in accordance with the disclosed embodiments. This PET scanning system 100 includes a total-body dynamic PET scanner 102, such as the recently developed 194 cm long total-body PET/CT scanner (uEXPLORER™) produced by the EXPLORER consortium, which is a multi-institutional group established to design, build and utilize the world's highest sensitivity PET scanners. (See Zhang X, et al. "Total-Body dynamic reconstruction and parametric imaging on the uEXPLORER." *J Nucl Med*, submitted.) During operation, total-body dynamic PET scanner 102 performs a high-temporal-resolution, total-body dynamic PET scan on a subject as an intravenously injected radioactive tracer propagates through the vascular system of the subject to produce PET projection data 106, which is stored in a data store 104. Next, a reconstruction processing system 108 applies a reconstruction technique to the PET projection data 106 to produce temporal frames 110, which illustrate the dynamic propagation of the radioactive tracer through the vascular system of the subject. These temporal frames 110 are stored in a data store 112 (which may be the same as data store 104). Finally, the system outputs the temporal frames through a display 114.

Figure 2:
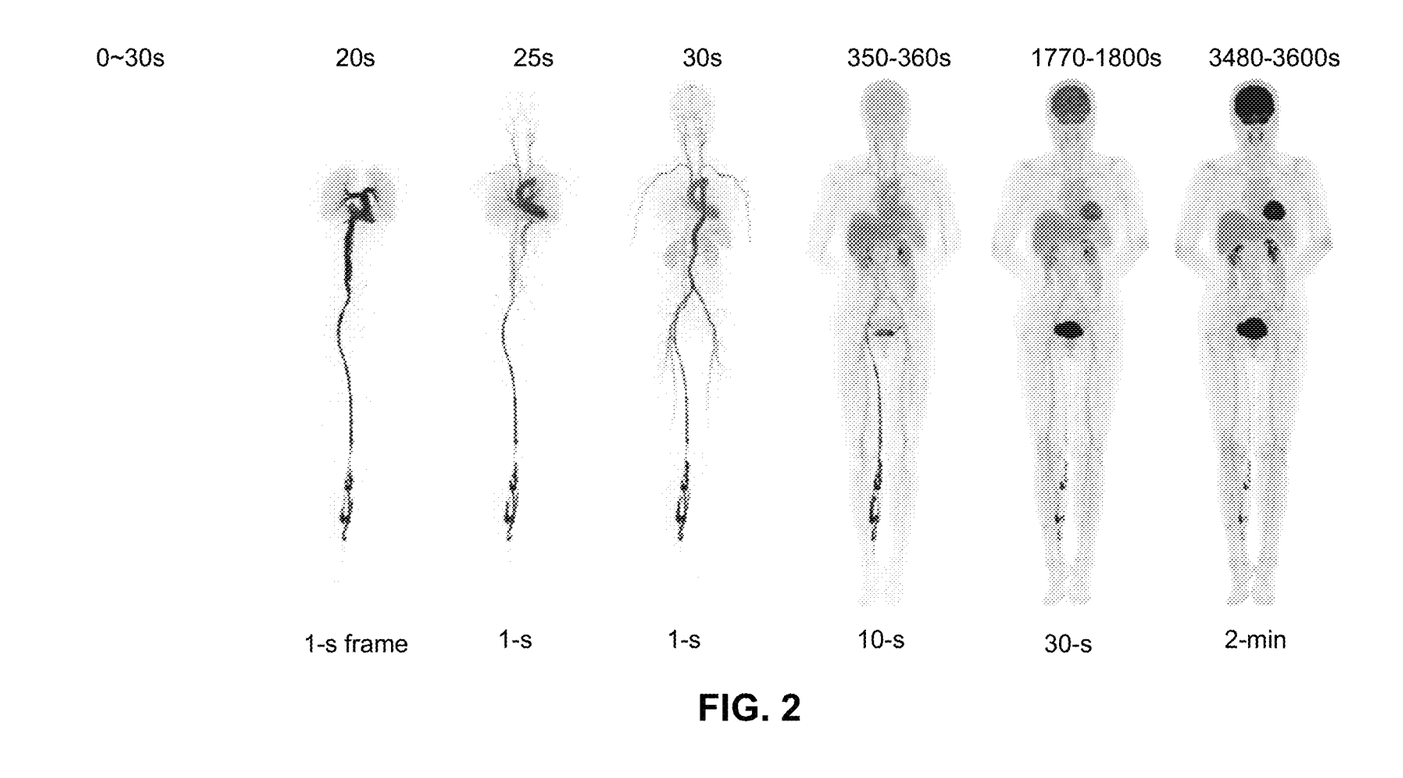
FIG. 2 presents images of tracer propagation produced through total-body parametric imaging and kernel-based reconstruction techniques in accordance with the disclosed embodiments.

This type of dynamic total-body scanner and associated high temporal resolution reconstruction technique can produce dramatic images (or videos) of the radioactive tracer propagating through the vascular system of a subject as is illustrated in FIG. 2. More specifically, FIG. 2 provides an anterior view of the subject as the radioactive tracer propagates from the subject's leg and into the subject's cardiovascular system before propagating throughout various organs in the subject's body. This process is described in more detail below.

Empirical Results

A total-body (TB) dynamic scan was performed for 60 minutes immediately after an intravenous injection of 256 MBq of $^{18}$F-fluorodeoxyglucose via a vein in the right leg of a healthy volunteer (60-year-old female), after obtaining informed consent. A total of ~61 billion prompt coincidences were recorded. To exploit the high temporal resolution of the scanner for capturing fast tracer uptake and cardiac motion, we divided the dataset into 0.1 second temporal frames and analyzed the data in the first minute and last minute of the scan. To reconstruct the high-temporal-resolution frames, we performed a kernel-based image reconstruction on the total-body dynamic scan. In this study, we reconstructed three composite frames (early 10 minute, middle 20 minute, and late 30 minute) to extract dynamic image features and used a Gaussian kernel function to construct the kernel matrix. The kernel matrix was then used to reconstruct the 0.1 second frames. All images were reconstructed into a 239×239×679 matrix with 2.85 mm cubic voxels. All quantitative corrections were included in the iterative reconstruction procedure. We also implemented a data-driven cardiac motion gating method, where the motion signal was extracted directly from the reconstructed image using a region of interest placed on the myocardium. The resulting estimated cardiac motion frequency was around 1.17 Hz (period 0.85 sec). A band pass filter (from 0.9 Hz to 1.3 Hz) was used to smooth the cardiac motion signal to facilitate cardiac gating.

Figure 3A:
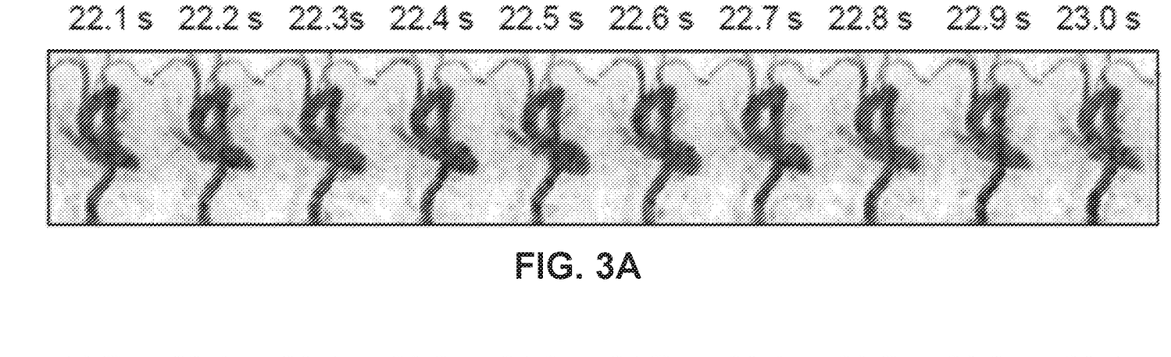
FIG. 3A presents reconstructed dynamic PET images comprising 10 consecutive 100 ms frames to visualize cardiac motion in accordance with the disclosed embodiments.
Figure 3B:
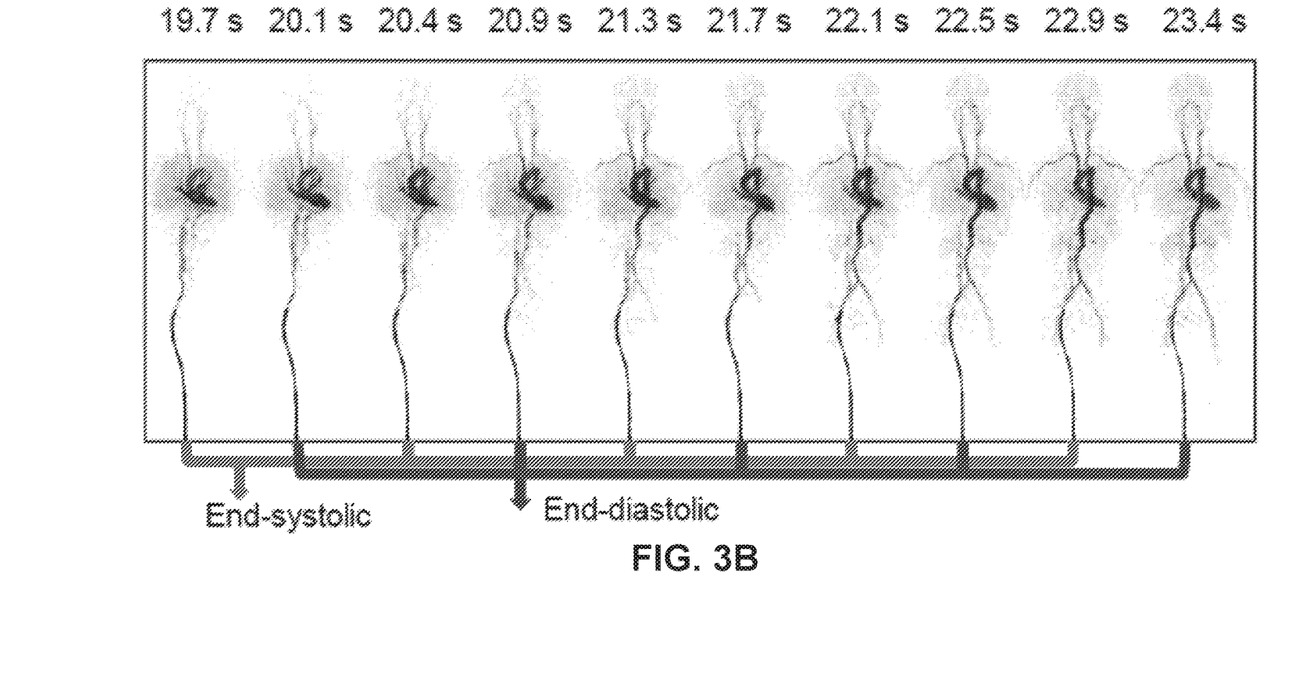
FIG. 3B presents selected PET images of 100 ms frames alternating between the end-diastolic and end-systolic phases of five cardiac cycles in accordance with the disclosed embodiments.

FIG. 3A shows resulting maximum intensity projections of the reconstructed dynamic PET images of 10 consecutive 100 ms frames to visualize the cardiac motion. FIG. 3B shows 10 selected 100 ms frames, alternating between end-diastolic and end-systolic phases of five cardiac cycles, to show the radiotracer bolus delivery and distribution within the whole body. Also, a full video with 100 ms temporal resolution was produced. Note that the number of detected true coincident events in each temporal frame is less than 1 million. Even at this low count level, the reconstructed images show good image quality. Changes in the cardiac blood pool are well captured by the 100 ms dynamic PET images, with clear delineation of the end-systolic and end-diastolic phases. The flow of the radiotracer as a result of cardiac contraction, which pumps the radiotracer bolus from the left ventricle (LV) to the aorta, from which it is distributed in the arterial tree, can be clearly observed.

Figure 3C:
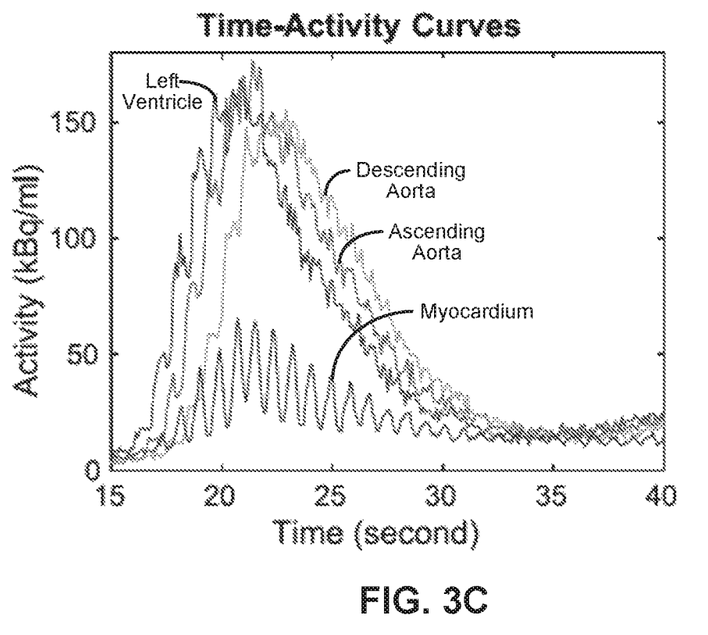
FIG. 3C presents a graph illustrating time-activity curves (TACs) obtained from 100 ms frames in accordance with the disclosed embodiments.
Figure 3D:
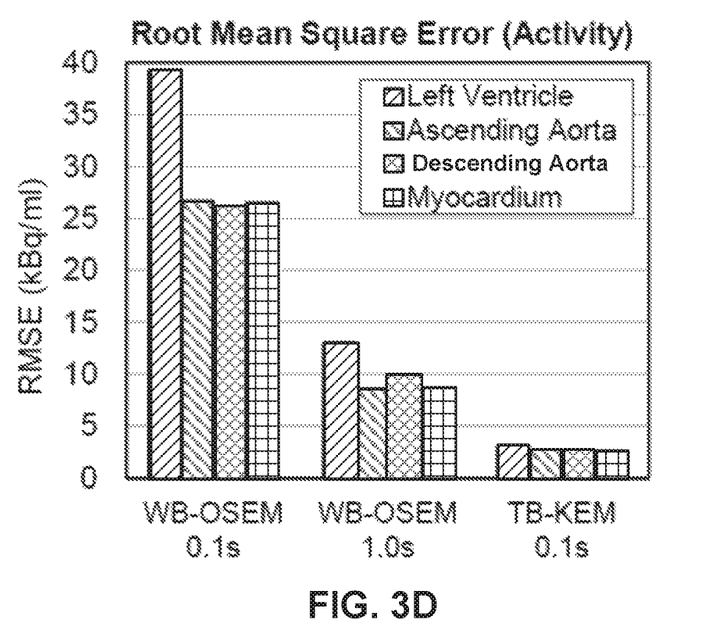
FIG. 3D presents a bar chart that compares root-mean-squared errors (RMSEs) between ordered-subset expectation maximization (OSEM) reconstructions (1 second and 0.1 seconds) and a kernel expectation maximization (KEM) reconstruction (0.1 second) in accordance with the disclosed embodiments.

FIG. 3C shows time-activity curves (TACs) in four regions of interest (ROIs) during the first minute after tracer injection. The four ROIs are drawn in the LV, descending aorta, ascending aorta, and myocardium. Besides the obvious time delay between the three blood curves, they also show a staircase pattern, because new blood enters the LV in the diastolic phase of the cardiac cycle and is pumped into the aorta in the systolic phase of the cardiac cycle. As a result, the radiotracer concentration in the LV only changes in the diastolic phase and remains nearly constant during the systolic phase, whereas the radiotracer concentration in the aorta changes in the systolic phase and remains nearly constant in the diastolic phase. This phenomenon is also evident in the images shown in FIG. 3B. Note that the TAC of the descending aorta is lower than those of the LV and ascending aorta, due to increased dispersion of the bolus at that point. Also, the myocardium TAC exhibits a clear cyclical rhythm from the heart beat, because we used a fixed ROI in which the blood fraction changes with cardiac cycle. All of these observations would not be possible at the lower temporal resolution previously used in dynamic PET imaging. To quantify the improvement over a standard whole-body (WB) scanner, we extracted events corresponding to one detector ring covering the heart region from the uEXPLORER data to mimic a WB scanner with an axial field of view of 24 cm. Using the first 120 seconds of data as the ground truth, we generated 30 noisy realizations of 0.1 second and 1 second scans by resampling the list mode data. The WB data was reconstructed using the standard ordered-subset EM (OSEM) algorithm. Voxel-wise root-mean-squared errors (RMSE) of the reconstructed images were calculated for the four ROIs and plotted in FIG. 3D. The RMSE of the proposed 0.1 second TB kernel-EM (TB-KEM) is about 10 times less than the 0.1 second WB scan, and about three times less than the one second WB scan.

These results demonstrate that, by combining the kernel-EM reconstruction with the EXPLORER scanner, we can obtain dynamic PET images at 100 ms temporal resolution with good quality. This high temporal resolution tracer imaging technique opens up opportunities for new applications, such as studying fast pharmacodynamics, using shorter-lived radionuclides (e.g., $^{82}$Rb, $^{13}$N, and $^{15}$O), and performing motion-frozen scans of the heart, lung, and gastrointestinal tract. Although many current clinical imaging systems, such as angiography, computerized tomography (CT), magnetic resonance imaging (MRI), and ultrasound, can locally perform fast imaging and provide specific anatomical or functional information, none of them can generate real-time molecular imaging of physiology and biochemistry processes with TB coverage. The quality of the 100 ms images is aided by the high contrast of activity in the vascular system. Note that the optimal temporal sampling and spatial resolution will be different for images of radiotracer activity widely distributed throughout tissues. Also, the image quality can be further improved by incorporating machine learning methods.

PET with high temporal resolution also has potential applications in the characterization of normal and abnormal brain function. Although functional MRI can detect changes associated with cerebral blood flow (CBF), our approach has the potential to directly measure the absolute value of CBF and the cerebral metabolic rate of oxygen. The advantage of CBF as determined with diffusible tracers in PET is that it measures blood flow at the nutrient capillary level (not only in large vessels). During the stimulation, parameters derived within a window of a second may show better correlation with postsynaptic activity and less hemodynamic lag. Moreover, these methods could be used to localize neural activity by correlating it with specific neurotransmitter activity. Furthermore, without the artifacts induced by cardiac and respiratory motion, ultrafast PET may allow analysis of metabolic processes within atherosclerotic plaques, and evaluate their distribution and characteristics throughout the cardiovascular system. Finally, high temporal resolution PET together with the TB coverage allows dynamic tracer studies of brain-heart and brain-gut interactions.

We next provide high-level flow charts for the various image-processing operations.

Process of Operation

Figure 4:
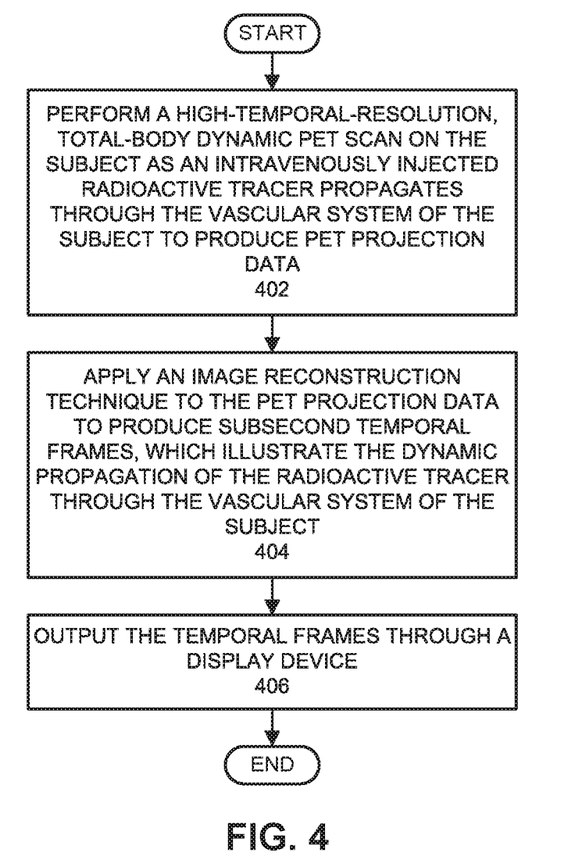
FIG. 4 presents a flow chart illustrating a process for performing ultra-fast tracer imaging in accordance with the disclosed embodiments.

FIG. 4 presents a flow chart illustrating a process for performing ultra-fast tracer imaging in accordance with the disclosed embodiments. During operation, the system performs a high-temporal-resolution, total-body dynamic PET scan on the subject as an intravenously injected radioactive tracer propagates through the vascular system of the subject to produce PET projection data (step 402). (Note that the optimal temporal sampling and spatial resolution will be different for images of radiotracer activity widely distributed throughout tissues. Moving to transport, biochemical reactions of metabolic processes, signal transduction and cell cycling of a wide array of biological functions will require optimization dependent on their respective time constants.) Next, the system applies an image reconstruction technique to the PET projection data to produce subsecond temporal frames, which illustrate the dynamic propagation of the radioactive tracer through the vascular system of the subject (step 404). Finally, the system outputs the temporal frames through a display device (step 406).

Figure 5:
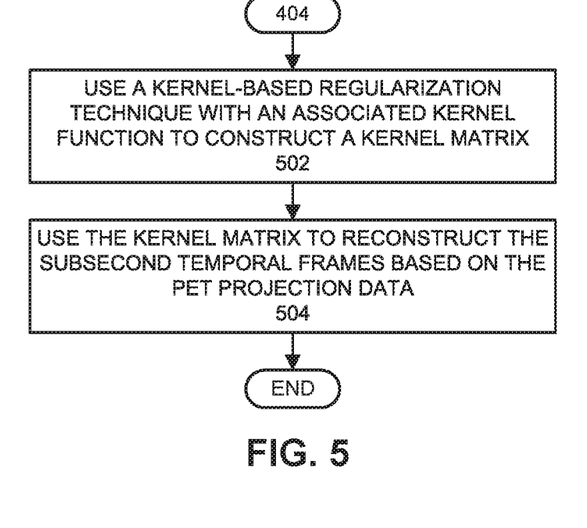
FIG. 5 presents a flow chart illustrating a process for applying a kernel-based regularization technique in accordance with the disclosed embodiments.

FIG. 5 presents a flow chart illustrating a process for applying a kernel-based regularization technique in accordance with the disclosed embodiments. (This flow chart illustrates in more detail the operations performed in step 404 of the flow chart in FIG. 4.) The system first uses an associated kernel function to construct a kernel matrix (step 502). Next, the system uses the kernel matrix to reconstruct the subsecond temporal frames based on the PET projection data (step 504).

Figure 6:
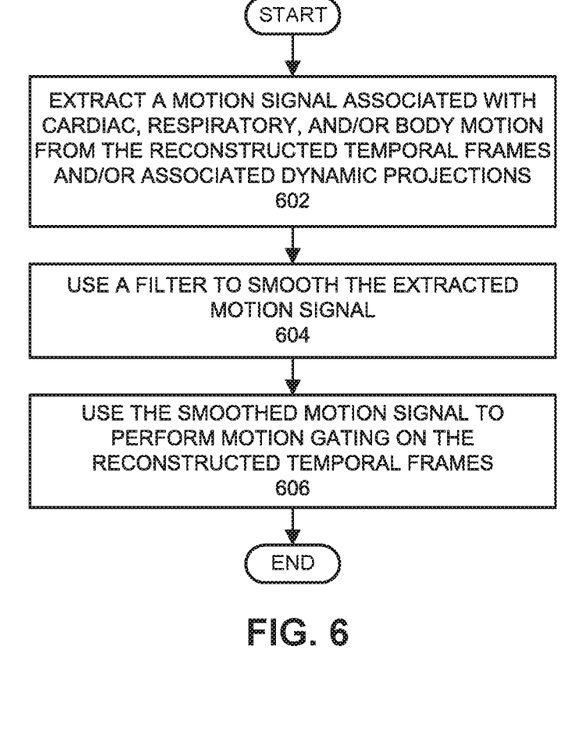
FIG. 6 presents a flow chart illustrating a process for performing cardiac gating based on high-temporal-resolution subsecond temporal frames in accordance with the disclosed embodiments.

FIG. 6 presents a flow chart illustrating a process for performing cardiac gating based on high temporal resolution of the subsecond temporal frames in accordance with the disclosed embodiments. First, the system extracts a motion signal associated with cardiac, respiratory, and/or body motion from the reconstructed temporal frames and/or associated dynamic projections (step 602). The system then uses a (linear or nonlinear) filter to smooth the extracted motion signal (step 604). Finally, the system uses the smoothed motion signal to perform motion gating on the reconstructed temporal frames (step 606).

Applications

The disclosed embodiments provide an ultra-high temporal resolution tracer imaging technique that opens up opportunities for new research and clinical applications related to the cardiovascular system, neurology and oncology. For example, accurate measurements of cardiac blood flow/perfusion are important for diagnosing heart disease, such as coronary artery disease, myocardium viability, etc. The high temporal sampling provided by this new technique can be used to track fast activity changes throughout the cardiovascular system, with intrinsic separation of diastolic and systolic phases without requiring cardiac or respiratory gating. Without the artifacts induced by cardiac and respiratory motion, ultrafast PET makes it possible to analyze metabolic processes within atherosclerotic plaques, and to evaluate their distribution and characteristics throughout the cardiovascular system.

The new technique can also be used to localize neural activity by correlating it with specific neurotransmitter activity.

Finally, the high temporal resolution PET provided by this new technique together with TB coverage facilitates dynamic tracer studies of brain-heart and brain-gut interactions.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for performing ultra-fast tracer imaging on a subject using positron emission tomography (PET), comprising:
   intravenously injecting a radioactive tracer into the subject;
   performing a high-temporal-resolution, total-body dynamic PET scan on the subject as the radioactive tracer propagates through the vascular system of the subject to produce PET projection data;
   applying an image reconstruction technique to the PET projection data to produce subsecond temporal frames that illustrate the dynamic propagation of the radioactive tracer through the vascular system of the subject, wherein applying the image reconstruction technique involves:
   using a kernel-based regularization technique with an associated kernel function to construct a kernel matrix; and
   using the kernel matrix to reconstruct the subsecond temporal frames based on the PET projection data; and
   outputting the temporal frames through a display device.

2. The method of claim 1, wherein the high temporal resolution of the subsecond temporal frames facilitates visualizing the dynamics of tracer propagation through the vascular system of the subject during individual heart beats.

3. The method of claim 1, wherein the subsecond temporal frames comprise 100 millisecond temporal frames.

4. The method of claim 1, wherein the reconstruction technique extracts dynamic image features in the temporal frames.

5. The method of claim 1, wherein applying the image reconstruction technique to the PET projection data involves using a statistically based technique to iteratively reconstruct the temporal frames from the PET projection data.

6. The method of claim 1, wherein the kernel-based regularization technique reconstructs a current temporal frame based on PET projection data associated with future temporal frames.

7. The method of claim 1, wherein the image reconstruction technique involves using a machine-learning-based de-noising technique to de-noise low-count images and/or iteratively reconstruct the temporal frames.

8. The method of claim 1, wherein the method further comprises:
   extracting a motion signal associated with cardiac, respiratory, and/or body motion from the reconstructed temporal frames and/or associated dynamic projections;
   using a filter to smooth the extracted motion signal; and
   using the smoothed motion signal to perform motion gating on the reconstructed temporal frames.

9. The method of claim 5, wherein the statistically based technique includes one or more of the following:
   a maximum-likelihood estimation technique;
   a penalized-likelihood estimation technique;
   a regularization technique; and
   a post-filtering technique.

10. A system that facilitates performing ultra-fast tracer imaging, comprising:
    a total-body dynamic PET scanner configured to perform a high-temporal-resolution, total-body dynamic PET scan on a subject as an intravenously injected radioactive tracer propagates through the vascular system of the subject to produce PET projection data;
    a processing module that applies an image reconstruction technique to the PET projection data to produce subsecond temporal frames that illustrate the dynamic propagation of the radioactive tracer through the vascular system of the subject, wherein applying the image reconstruction technique involves:
       using a kernel-based regularization technique with an associated kernel function to construct a kernel matrix; and
       using the kernel matrix to reconstruct the subsecond temporal frames based on the PET projection data; and
    a display device configured to output the temporal frames.

11. The system of claim 10, wherein the high temporal resolution of the subsecond temporal frames facilitates visualizing the dynamics of tracer propagation through the vascular system of the subject during individual heart beats.

12. The system of claim 10, wherein the subsecond temporal frames comprise 100 millisecond temporal frames.

13. The system of claim 10, wherein the processing module extracts dynamic image features in the temporal frames.

14. The system of claim 10, wherein while applying the image reconstruction technique to the PET projection data, the processing module uses a statistically based technique to iteratively reconstruct the temporal frames from the PET projection data.

15. The system of claim 10, wherein while applying the image reconstruction technique to the PET projection data, the processing module:
    uses a kernel-based regularization technique with an associated kernel function to construct a kernel matrix; and
    uses the kernel matrix to reconstruct the subsecond temporal frames based on the PET projection data.

16. The system of claim 10, wherein while using the kernel-based regularization technique, the processing module reconstructs a current temporal frame based on PET projection data associated with future temporal frames.

17. The system of claim 10, wherein while applying the image reconstruction technique, the processing module uses a machine-learning-based de-noising technique to de-noise low-count images and/or iteratively reconstruct the temporal frames.

18. The system of claim 10, wherein the processing module is additionally configured to:
    extract a motion signal associated with cardiac, respiratory, and/or body motion from the reconstructed temporal frames and/or associated dynamic projections;
    use a filter to smooth the extracted motion signal; and
    use the smoothed motion signal to perform motion gating on the reconstructed temporal frames.

19. The system of claim 14, wherein the statistically based technique includes one or more of the following:
    a maximum-likelihood estimation technique;
    a penalized-likelihood estimation technique;
    a regularization technique; and
    a post-filtering technique.

20. A non-transitory computer-readable storage medium storing instructions that when executed by a computer cause the computer to perform a method for performing ultra-fast tracer imaging on a subject using positron emission tomography (PET), the method comprising:
    performing a high-temporal-resolution, total-body dynamic PET scan on the subject as an intravenously injected radioactive tracer propagates through the vascular system of the subject to produce PET projection data;
    applying an image reconstruction technique to the PET projection data to produce subsecond temporal frames that illustrate the dynamic propagation of the radioactive tracer through the vascular system of the subject, wherein applying the image reconstruction technique involves:
       using a kernel-based regularization technique with an associated kernel function to construct a kernel matrix; and
       using the kernel matrix to reconstruct the subsecond temporal frames based on the PET projection data; and
    outputting the temporal frames through a display device.

21. The non-transitory computer-readable storage medium of claim 20, wherein the high temporal resolution of the subsecond temporal frames facilitates visualizing the dynamics of tracer propagation through the vascular system of the subject during individual heart beats.

22. The non-transitory computer-readable storage medium of claim 20, wherein the subsecond temporal frames comprise 100 millisecond temporal frames.

23. The non-transitory computer-readable storage medium of claim 20, wherein the reconstruction technique extracts dynamic image features in the temporal frames.

24. The non-transitory computer-readable storage medium of claim 20, wherein applying the image reconstruction technique to the PET projection data involves using a statistically based technique to iteratively reconstruct the temporal frames from the PET projection data.

25. The non-transitory computer-readable storage medium of claim 20, wherein applying the image reconstruction technique to the PET projection data involves:
  using a kernel-based regularization technique with an associated kernel function to construct a kernel matrix; and
  using the kernel matrix to reconstruct the subsecond temporal frames based on the PET projection data.

26. The non-transitory computer-readable storage medium of claim 20, wherein the kernel-based regularization technique reconstructs a current temporal frame based on PET projection data associated with future temporal frames.

27. The non-transitory computer-readable storage medium of claim 20, wherein the image reconstruction technique involves using a machine-learning-based de-noising technique to de-noise low-count images and/or iteratively reconstruct the temporal frames.

28. The non-transitory computer-readable storage medium of claim 20, wherein the method further comprises:
  extracting a motion signal associated with cardiac, respiratory, and/or body motion from the reconstructed temporal frames and/or associated dynamic projections;
  using a filter to smooth the extracted motion signal; and
  using the smoothed motion signal to perform
  motion gating on the reconstructed temporal frames.

29. The non-transitory computer-readable storage medium of claim 24, wherein the statistically based technique includes one or more of the following:
  a maximum-likelihood estimation technique;
  a penalized-likelihood estimation technique;
  a regularization technique; and
  a post-filtering technique.

* * * * *